US012613540B2

(12) United States Patent
Cui et al.

(10) Patent No.: US 12,613,540 B2
(45) Date of Patent: Apr. 28, 2026

(54) METHOD FOR PROTECTING RADIO FREQUENCY OPERATION OBJECT FROM DATA ABNORMALITY, AND RADIO FREQUENCY HOST AND STORAGE MEDIUM

(71) Applicant: HANGZHOU BRONCUS MEDICAL CO., LTD., Hangzhou (CN)

(72) Inventors: Changjie Cui, Hangzhou (CN); Hong Xu, Hangzhou (CN)

(73) Assignee: Hangzhou Broncus Medical Co., Ltd., Hangzhou (CN)

( * ) Notice: Subject to any disclaimer, the term of this patent is extended or adjusted under 35 U.S.C. 154(b) by 329 days.

(21) Appl. No.: 18/346,063

(22) Filed: Jun. 30, 2023

(65) Prior Publication Data

US 2023/0341879 A1 Oct. 26, 2023

Related U.S. Application Data

(63) Continuation of application No. PCT/CN2021/142753, filed on Dec. 29, 2021.

(30) Foreign Application Priority Data

Dec. 31, 2020 (CN) .......................... 202011641965.0

(51) Int. Cl.
A61B 18/14        (2006.01)
G05D 23/19        (2006.01)
A61B 18/00        (2006.01)

(52) U.S. Cl.
CPC .......... *G05D 23/1917* (2013.01); *A61B 18/14* (2013.01); *A61B 2018/00011* (2013.01);
(Continued)

(58) Field of Classification Search
CPC ............... A61B 18/1233; A61B 18/14; A61B 2018/00011; A61B 2018/00577;
(Continued)

(56) References Cited

U.S. PATENT DOCUMENTS 5,334,193 A * 8/1994 Nardella ............ A61B 18/1492
                                                          606/41
5,342,357 A    8/1994 Nardella
                        (Continued)

FOREIGN PATENT DOCUMENTS

CN        110074856        8/2019
CN        110897710        3/2020
                (Continued)

OTHER PUBLICATIONS

International Search Report and Written Opinion, issued in the corresponding PCT application No. PCT/CN2021/142753, dated Mar. 14, 2022, 17 pages (translation enclosed).
(Continued)

*Primary Examiner* — Michael F Peffley

(57) ABSTRACT

A method for protecting a radio frequency operation object from data abnormality, a radio frequency host and a storage medium are provided. The method for protecting a radio frequency operation object from data abnormality includes:
(Continued)

determining a data protection mode of the radio frequency operation object, which includes a uni-protection mode and a dual-protection mode; when the data protection mode is the dual-protection mode, detecting, in real time, first and second physical characteristic data of the radio-frequency operation object corresponding to the dual-protection mode; and when the values of the first and second physical characteristic data are beyond their respective preset numerical ranges, adjusting the values of the first and second physical characteristic data respectively according to priorities of protection against the first and second physical characteristic data, to make the values of the first and second physical characteristic data be both within their respective numerical ranges.

8 Claims, 3 Drawing Sheets

(52) U.S. Cl.
CPC ............... *A61B 2018/00577* (2013.01); *A61B 2018/00744* (2013.01); *A61B 2018/00791* (2013.01); *A61B 2018/00875* (2013.01)

(58) Field of Classification Search
CPC ........... A61B 2018/00702; A61B 2018/00714; A61B 2018/00744; A61B 2018/00755; A61B 2018/00791; A61B 2018/00863; A61B 2018/00875
See application file for complete search history.

(56) References Cited

U.S. PATENT DOCUMENTS

| | | | | |
|---|---|---|---|---|
| 5,540,684 | A * | 7/1996 | Hassler, Jr. ......... | A61B 18/1206 606/51 |
| 6,537,272 | B2 * | 3/2003 | Christopherson ...... | A61B 18/14 606/41 |
| 8,211,100 | B2 * | 7/2012 | Podhajsky ......... | A61B 18/1206 606/34 |
| 2002/0058933 | A1 | 5/2002 | Christopherson et al. | |
| 2004/0215183 | A1 | 10/2004 | Hoey et al. | |
| 2010/0179535 | A1 | 7/2010 | Podhajsky et al. | |

FOREIGN PATENT DOCUMENTS

| | | |
|---|---|---|
| CN | 112716594 | 4/2021 |
| CN | 112791262 | 5/2021 |
| EP | 0694291 B1 | 10/2001 |

OTHER PUBLICATIONS

First Chinese Office Action and Search Report, issued in the corresponding Chinese patent application No. 202011641965.0, dated Oct. 9, 2021, 19 pages (translation enclosed).
Office Action Dated Mar. 11, 2025 for Corresponding Indian Patent Application No. 202327048493.

* cited by examiner

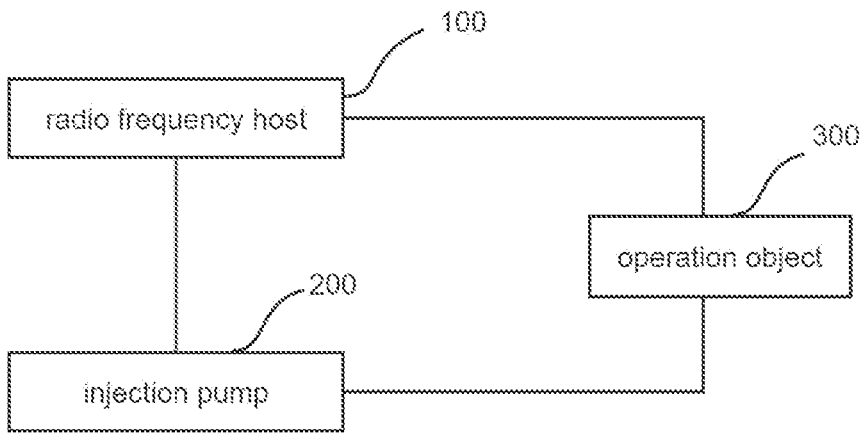

FIG. 1

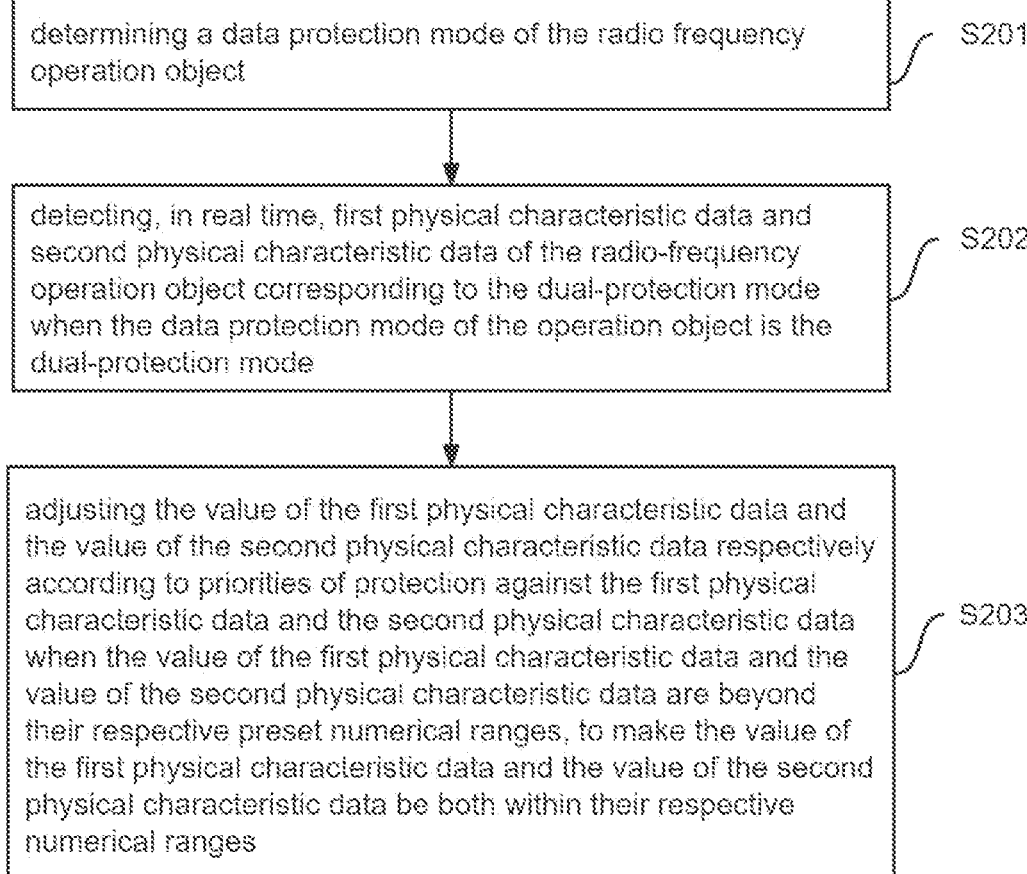

| determining a data protection mode of the radio frequency operation object | S201 |

| detecting, in real time, first physical characteristic data and second physical characteristic data of the radio-frequency operation object corresponding to the dual-protection mode when the data protection mode of the operation object is the dual-protection mode | S202 |

| adjusting the value of the first physical characteristic data and the value of the second physical characteristic data respectively according to priorities of protection against the first physical characteristic data and the second physical characteristic data when the value of the first physical characteristic data and the value of the second physical characteristic data are beyond their respective preset numerical ranges, to make the value of the first physical characteristic data and the value of the second physical characteristic data be both within their respective numerical ranges | S203 |

FIG. 2

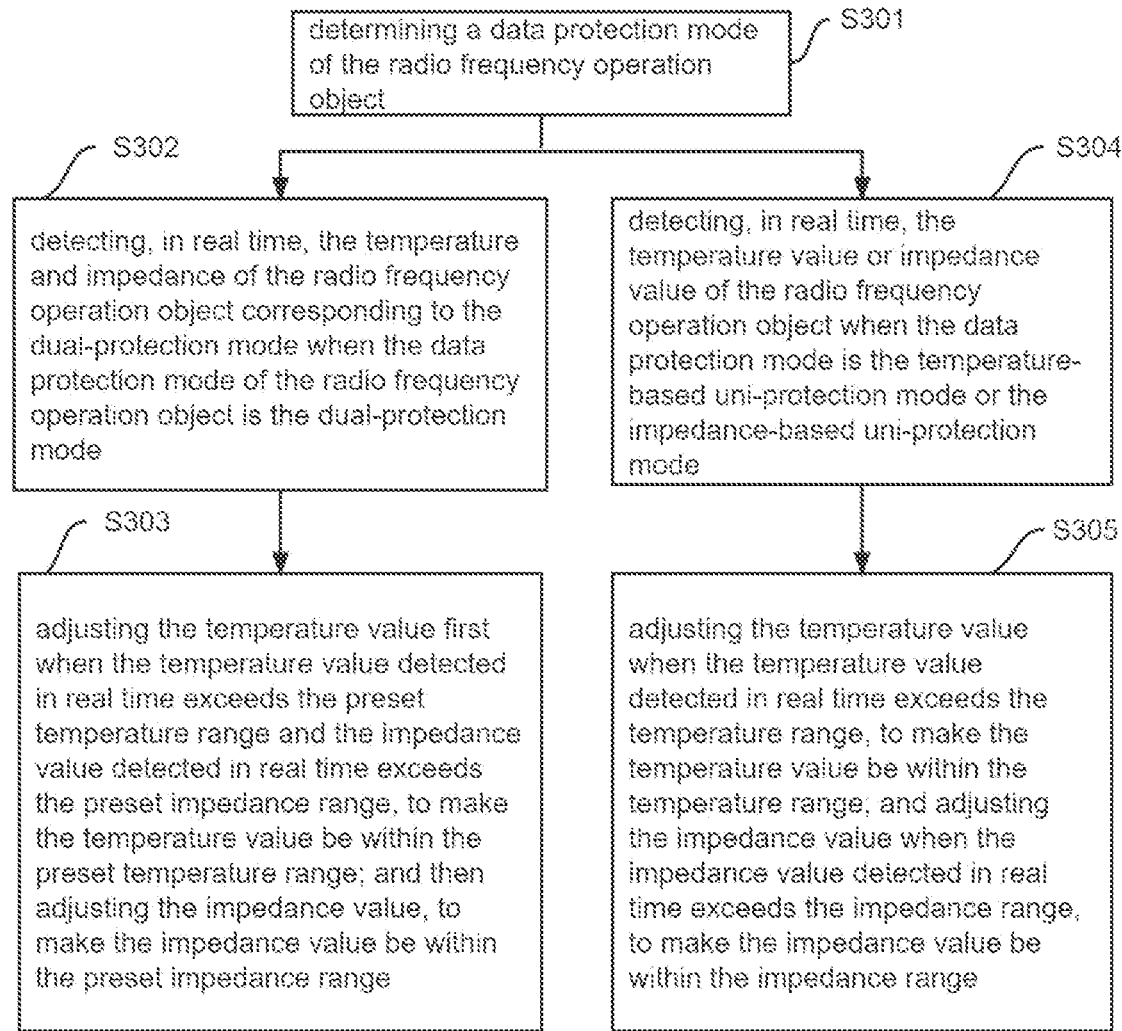

determining a data protection mode of the radio frequency operation object ⌐ S301

S302 ⌐ detecting, in real time, the temperature and impedance of the radio frequency operation object corresponding to the dual-protection mode when the data protection mode of the radio frequency operation object is the dual-protection mode

⌐ S304 detecting, in real time, the temperature value or impedance value of the radio frequency operation object when the data protection mode is the temperature-based uni-protection mode or the impedance-based uni-protection mode

⌐ S303 adjusting the temperature value first when the temperature value detected in real time exceeds the preset temperature range and the impedance value detected in real time exceeds the preset impedance range, to make the temperature value be within the preset temperature range; and then adjusting the impedance value, to make the impedance value be within the preset impedance range

⌐ S305 adjusting the temperature value when the temperature value detected in real time exceeds the temperature range, to make the temperature value be within the temperature range, and adjusting the impedance value when the impedance value detected in real time exceeds the impedance range, to make the impedance value be within the impedance range

FIG. 3

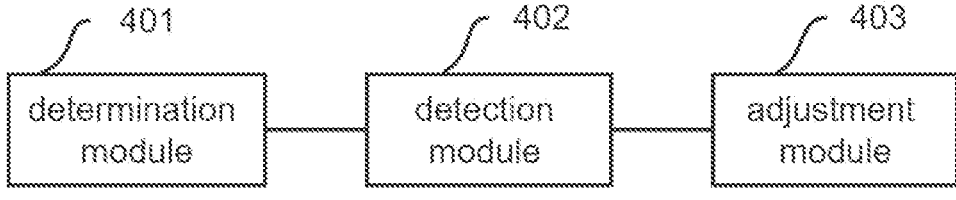

⌐ 401     ⌐ 402     ⌐ 403 determination module — detection module — adjustment module

FIG. 4

METHOD FOR PROTECTING RADIO FREQUENCY OPERATION OBJECT FROM DATA ABNORMALITY, AND RADIO FREQUENCY HOST AND STORAGE MEDIUM

CROSS-REFERENCE TO RELATED APPLICATIONS

The present application is a Continuation Application of PCT Application No. PCT/CN2021/142753, filed on Dec. 29, 2021, which claims the priority of Chinese Patent Application No. 202011641965.0, filed on Dec. 31, 2020, the entire contents of which are hereby incorporated by reference.

TECHNICAL FIELD

Embodiments of the present disclosure relate to the field of electronic technology, and particularly to a method for protecting a radio frequency operation object from data abnormality, a radio frequency host, and a computer readable storage medium.

DESCRIPTION OF THE PRIOR ART

In a radio frequency operation, the physical characteristic parameters of a radio frequency operation object may change with the progress of the radio frequency operation. If they are not controlled in time, damages will be caused to the radio frequency operation object, and malfunctions of the radio frequency host and other devices may be incurred, resulting in abnormal radio frequency operation and further possible injuries to a user undergoing the radio frequency operation.

In the prior art, the physical characteristic parameters of the radio frequency operation object are often empirically adjusted by an operator. However, this processing method is less accurate, and fails to effectively protect the radio frequency operation object, thus reducing the success rate and safety of the radio frequency operation.

SUMMARY OF THE DISCLOSURE

Technical Problem

Embodiments of the present disclosure provide a method for protecting a radio frequency operation object from data abnormality, a radio frequency host, and a computer readable storage medium. By virtue of the present disclosure, the automatic and accurate adjustment of abnormal physical characteristic parameters of the radio frequency operation object is realized, the radio frequency operation object is effectively protected, and the success rate and safety of the radio frequency operation are improved.

Technical Solution

In an aspect, an embodiment of the present disclosure provides a method for protecting a radio frequency operation object from data abnormality. The method includes:

determining a data protection mode of the radio frequency operation object, wherein the data protection mode includes a uni-protection mode and a dual-protection mode; if the data protection mode is the dual-protection mode, detecting, in real time, first physical characteristic data and second physical characteristic data of the radio frequency operation object corresponding to the dual-protection mode; and when the value of the first physical characteristic data and the value of the second physical characteristic data are respectively beyond their respective preset numerical ranges, adjusting the value of the first physical characteristic data and the value of the second physical characteristic data respectively according to the priorities of protection against the first physical characteristic data and the second physical characteristic data, such that the value of the first physical characteristic data and the value of the second physical characteristic data are both within their respective preset numerical ranges.

In an aspect, an embodiment of the present disclosure further provides a radio frequency host. The radio frequency host includes:

a determination module, configured to determine a data protection mode of a radio frequency operation object, wherein the data protection mode includes a uni-protection mode and a dual-protection mode; a detection module, configured to detect, in real time, first physical characteristic data and second physical characteristic data of the radio-frequency operation object corresponding to the dual-protection mode, if the data protection mode is the dual-protection mode; and an adjustment module, configured to adjust the value of the first physical characteristic data and the value of the second physical characteristic data respectively according to the priorities of protection against the first physical characteristic data and the second physical characteristic data, when the value of the first physical characteristic data and the value of the second physical characteristic data are respectively beyond their respective preset numerical ranges, such that the value of the first physical characteristic data and the value of the second physical characteristic data are both within their respective preset numerical ranges.

In an aspect, an embodiment of the present disclosure further provides a radio frequency host. The radio frequency host includes:

a storage and a processor, wherein the storage stores an executable program code; and the processor is coupled to the storage, and configured to call the executable program code stored in the storage, and implement the method for protecting a radio frequency operation object from data abnormality as described above.

In an aspect, an embodiment of the present disclosure further provides a computer readable storage medium storing a computer program. When the computer program is executed by a processor, the method for protecting a radio frequency operation object from data abnormality as described above is implemented.

Beneficial Effects

As can be known from the above embodiments of the present disclosure, if the data protection mode of the radio frequency operation object is the dual-protection mode, the first physical characteristic data and the second physical characteristic data of the radio frequency operation object corresponding to the dual-protection mode are detected in real time; and when the value of the first physical characteristic data and the value of the second physical characteristic data are respectively beyond their respective preset numerical ranges, the value of the first physical characteristic data and the value of the second physical characteristic data are adjusted respectively according to the priorities of protection against the first physical characteristic data and the second physical characteristic data, such that the value of the first physical characteristic data and the value of the second physical characteristic data are both within their respective preset numerical ranges. Through the dual adjustment of two physical characteristic data of the radio frequency operation object in sequence, the success rate of the radio frequency operation is improved, and equipment damages and personal injuries caused by data abnormality in the radio frequency operation are avoided, thereby improving the safety of the radio frequency operation.

BRIEF DESCRIPTION OF DRAWINGS

In order to describe the technical solutions according to the embodiments of the present disclosure or in the prior art more clearly, the drawings needed to be used in the embodiments or in the prior art will be described briefly below. Apparently, the drawings in the following description show some embodiments of the present application. Other drawings can be obtained by persons of ordinary skill in the art based on these drawings without creative efforts.

FIG. 1 is a schematic diagram showing an application scenario of a method for protecting a radio frequency operation object from data abnormality provided in an embodiment of the present disclosure;

FIG. 2 is a schematic flow chart of a method for protecting a radio frequency operation object from data abnormality provided in an embodiment of the present disclosure;

FIG. 3 is a schematic flow chart of a method for protecting a radio frequency operation object from data abnormality provided in another embodiment of the present disclosure;

FIG. 4 shows a structural schematic diagram of a radio frequency host provided in an embodiment of the present disclosure.

DESCRIPTION OF EMBODIMENTS

Figure 5:
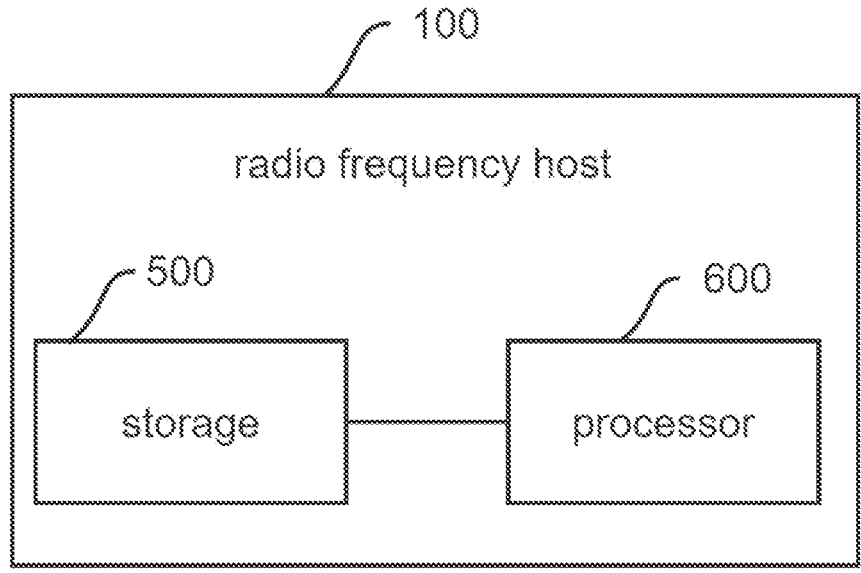
FIG. 5 shows a structural schematic diagram of a radio frequency host provided in another embodiment of the present disclosure.

In order to make the objects, technical solutions and advantages of the embodiments of the present disclosure clearer, the technical solutions according to the embodiments of the present disclosure will be clearly and completely described with reference to drawings in the embodiments of the present disclosure. Apparently, the embodiments described are merely some embodiments, but not all of the embodiments of the present application. All other embodiments obtained by ordinary persons skilled in the art based on the embodiments of the present disclosure without creative efforts shall fall within the protection scope of the present disclosure.

FIG. 1 is a schematic diagram showing an application scenario of a method for protecting a radio frequency operation object from data abnormality provided in an embodiment of the present disclosure. The method for protecting a radio frequency operation object from data abnormality is applicable in a radio frequency operation process, to adjust the temperature and/or impedance of the radio frequency operation object, and improve the success rate and safety of the radio frequency operation.

Specifically, as shown in FIG. 1, a radio frequency host 100, an injection pump 200 and a radio frequency operation object 300 are connected to each other, to form a radio frequency operation system. When a radio frequency operation is performed, the radio frequency host 100 transmits a radio frequency signal by a radio frequency generator, which is acted on an indicated position on the radio frequency operation object 300 by a radio frequency probe of the radio frequency host. With the characteristic of the indicated position on the radio frequency operation object 300 changes, physical characteristic data of the radio frequency operation object 300 detected by a detector in the radio frequency host 100 also changes. The injection pump 200 is provided with an injection unit, which injects, to the indicated position (that is, the operation position) on the radio frequency operation object 300, a cooling medium having cooling effect, under the control of the injection pump 200, The cooling medium is generally a liquid, and the physical characteristics of the operation position can be adjusted by adjusting the injection volume of the liquid. The liquid is safe and harmless, for example, it may be physiological saline. Specifically, the injection volume can be adjusted by controlling the injection flow rate. The radio frequency host 100 and the injection pump 200 are connected to form a radio frequency operation system. After connection, the radio frequency host 100 becomes a master device and the injection pump 200 becomes a slave device in the radio frequency operation system. The injection pump 200 is controlled by a controller in the radio frequency host 100 to perform the injection operation. The radio frequency operation object 300 can be any object in need of the radio frequency operation. For example, when the radio frequency host 300 is a radio frequency ablation instrument, the radio frequency operation object can be an animal with abnormal tissues in the body that needs to be ablated.

FIG. 2 is a schematic flow chart of a method for protecting a radio frequency operation object from data abnormality provided in an embodiment of the present disclosure. The method is applicable to the radio frequency host as shown in FIG. 1. As shown in FIG. 2, the method specifically includes the following steps:

Step S201: determining a data protection mode of the radio frequency operation object.

The data protection mode includes a uni-protection mode and a dual-protection mode. The uni-protection mode includes a temperature-based uni-protection mode and an impedance-based uni-protection mode. The dual-protection mode is a temperature- and impedance-based dual-protection mode.

Step S202: detecting, in real time, first physical characteristic data and second physical characteristic data of the radio-frequency operation object corresponding to the dual-protection mode, when the data protection mode of the radio frequency operation object is the dual-protection mode.

Specifically, if the data protection mode of the radio frequency operation object is the dual-protection mode, that is, the temperature- and impedance-based dual-protection mode, the first physical characteristic data is the temperature data, the second physical characteristic data is the impedance data, the first numerical range is a normal range of the temperature value, preferably, 34 to 42° C.; and the second numerical range is a normal range of the impedance value, preferably, 250-350 ohm.

Further, the acquired temperature value is compared with the corresponding first numerical range, and the acquired impedance value is compared with the corresponding second numerical range.

If the temperature value is greater than a maximum value of the first numerical range, or the temperature value is less than a minimum value of the first numerical range, the temperature value is determined as beyond the first numerical range.

If the impedance value is greater than a maximum value of the second numerical range, or the impedance value is less than a minimum value of the second numerical range, the impedance value is determined as beyond the second numerical range.

Step S203: adjusting the value of the first physical characteristic data and the value of the second physical characteristic data respectively according to the priorities of protection against the first physical characteristic data and the second physical characteristic data, when the value of the first physical characteristic data and the value of the second physical characteristic data are both beyond their respective preset numerical ranges, to make the value of the first physical characteristic data and the value of the second physical characteristic data both fall within their respective numerical ranges.

If the temperature value is greater than the maximum value of the first numerical range, or the temperature value is less than the minimum value of the first numerical range; and the impedance value is greater than the maximum value of the second numerical range, or the impedance value is less than the minimum value of the second numerical range, then it is determined that the temperature value and the impedance value are both beyond their respective preset numerical ranges.

The priority of protection against the temperature is higher than the priority of protection against the impedance. That is, the priority of protection against the temperature of the radio frequency operation object is higher than the priority of protection against the impedance of the radio frequency operation object. Therefore, the temperature is adjusted first, after the temperature is within the preset first numerical range; the impedance is adjusted then, to make the impedance be within the preset second numerical range on the premise that the temperature is maintained within the temperature range.

It should be noted that if only the temperature is beyond the first numerical range, and the impudence is not beyond the second numerical range, the temperature value is adjusted, to make the temperature be within the first numerical range. If only the impedance is beyond the second numerical range, and the temperature is not beyond the first numerical range, the impedance value is adjusted, to make the impedance be within the second numerical range.

In the embodiment of the present disclosure, if the data protection mode of the radio frequency operation object is the dual-protection mode, the first physical characteristic data and the second physical characteristic data of the radio frequency operation object corresponding to the dual-protection mode are detected in real time. When the value of the first physical characteristic data and the value of the second physical characteristic data are respectively beyond their respective preset numerical ranges, the value of the first physical characteristic data and the value of the second physical characteristic data are adjusted respectively according to the priorities of protection against the first physical characteristic data and the second physical characteristic data, to make the value of the first physical characteristic data and the value of the second physical characteristic data be both within their respective preset numerical ranges. Through the dual adjustment of two physical characteristic data of the radio frequency operation object in sequence, the success rate of the radio frequency operation is improved, and equipment damages and personal injuries caused by data abnormality in the radio frequency operation are avoided, thereby improving the safety of the radio frequency operation.

FIG. 3 is a schematic flow chart of implementing a method for protecting a radio frequency operation object from data abnormality provided in another embodiment of the present disclosure. The method is applicable to the radio frequency host as shown in FIG. 1. As shown in FIG. 3, the method specifically includes the following steps:

Step S301: determining a data protection mode of the radio frequency operation object.

Position information is acquired, and it is determined whether the data protection mode is set by a user. If the data protection mode is not set by a user, the data protection mode is a default temperature- and impedance-based dual-protection mode. If the data protection mode is set by a user, the data protection mode is determined to be one of a temperature-based uni-protection mode, an impedance-based uni-protection mode, and a temperature- and impedance-based dual-protection mode according to the user setting.

Temperature value or impedance value of the radio frequency operation object being too high will cause irreversible damage to the radio frequency operation object, and particularly the temperature value is a key direction of protection.

Step S302: detecting, in real time, the temperature and impedance of the radio frequency operation object corresponding to the dual-protection mode, if the data protection mode of the radio frequency operation object is the dual-protection mode.

Further, the acquired temperature value of the radio frequency operation object is compared with a preset first numerical range. The first numerical range is a temperature range. If the temperature value of the radio frequency operation object exceeds the temperature range, it needs to be adjusted.

The acquired impedance value of the radio frequency operation object is compared with a preset second numerical range. The second numerical range is an impedance range. If the impedance value of the radio frequency operation object exceeds the impedance range, it needs to be adjusted.

If the temperature value is greater than a maximum value of the first numerical range, or the temperature value is less than a minimum value of the first numerical range, the temperature value detected in real time is determined as beyond the temperature range.

If the impedance value is greater than a maximum value of the second numerical range, or the impedance value is less than a minimum value of the second numerical range, the impedance value detected in real time is determined as beyond the impedance range.

Step S303: adjusting the temperature value first when the temperature value detected in real time exceeds the preset temperature range, and the impedance value detected in real time exceeds the preset impedance range, to make the temperature value be within the preset temperature range; and then adjusting the impedance value, to make the impedance value be within the preset impedance range.

Specifically, the priority of protection against the temperature is higher than the priority of protection against the impedance. The temperature value is adjusted first, wherein the temperature value is controlled by controlling the injection flow rate of the injection pump and the output power of the radio frequency signal in combination.

The injection pump is controlled to inject a cooling medium to the radio frequency operation object at a preset temperature adjustment-intended injection flow rate, to make the temperature value of the radio frequency operation object be within the preset first numerical range, that is, the preset temperature range. In the radio frequency host or the injection pump, a corresponding relationship between the adjustment amount of the temperature adjustment-intended injection flow rate and the adjustment amount of the temperature is preset. That is, when a present injection flow rate is adjusted by an adjustment amount, the temperature will be accordingly adjusted by an adjustment amount. When the present temperature is intended to be adjusted to a target temperature, the adjustment amount of the injection flow rate that needs to be changed can be determined by querying the corresponding relationship.

Further, if the temperature value detected in real time is greater than the maximum value of the temperature range, the preset temperature adjustment-intended injection flow rate is greater than the present injection flow rate. After the target temperature to which the present temperature is intended to be reduced is determined, an increment of the injection flow rate is obtained by querying the corresponding relationship according to a difference between the present temperature and the target temperature. The present injection flow rate plus the increment is the temperature adjustment-intended injection flow rate. The injection pump is controlled to inject the liquid to the radio frequency operation object at the temperature adjustment-intended injection flow rate. Similarly, if the temperature value detected in real time is less than the minimum value of the temperature range, the preset temperature adjustment-intended injection flow rate is less than the present injection flow rate. A decrement of the injection flow rate is obtained by querying the corresponding relationship. The cooling medium is injected at an injection flow rate decreased by the decrement.

If the temperature value of the radio frequency operation object is still beyond the temperature range when the injection flow rate of the injection pump reaches a limit value for temperature adjustment, the control of the injection flow rate is stopped, and the temperature is further adjusted by controlling the output power of the radio frequency signal, to make the temperature value of the radio frequency operation object be within the temperature range. The limit value for temperature adjustment is less than the maximum injection flow rate of the injection pump, and can be preset according to actual needs in temperature control. The specific numerical is not limited here. The output power can be adjusted as follows. The voltage and current in the radio frequency circuit are detected, and multiplied to obtain an actual power. According to a preset power algorithm, a corresponding relationship between the adjustment amount of the output power and the adjustment amount of the actual power is calculated. Then the output power is adjusted, and in turn the actual power is accordingly adjusted, to achieve the purpose of temperature control.

Then the impedance value is adjusted. The impedance is adjusted merely by adjusting the injection flow rate of the injection pump. On the premise that the temperature value is maintained within the temperature range, the injection pump is further controlled to inject the cooling medium to the radio frequency operation object at a preset impedance adjustment-intended injection flow rate, to make the impedance value of the radio frequency operation object be within the preset second numerical range. The adjustment of the injection flow rate is the same as that in the adjustment of the temperature, and can be performed with reference to the descriptions above, which will not be repeated here.

The cooling medium injected by the injection pump to the radio frequency operation object is a temperature lowering liquid, for example, physiological saline.

Step S304: detecting, in real time, the temperature value or impedance value of the radio frequency operation object, when the data protection mode is the temperature-based uni-protection mode or the impedance-based uni-protection mode.

If the data protection mode is the temperature-based uni-protection mode, the temperature value of the radio frequency operation object is detected in real time.

If the data protection mode is the impedance-based uni-protection mode, the impedance value of the radio frequency operation object is detected in real time.

Step S305: adjusting the temperature value when the temperature value detected in real time exceeds the temperature range, to make the temperature value be within the temperature range; and adjusting the impedance value when the impedance value detected in real time exceeds the impedance range, to make the impedance value be within the impedance range.

The specific adjustment ways are the same as the temperature and impedance adjustment methods in the temperature- and impedance-based double protection mode. The temperature is adjusted first by adjusting the injection flow rate of the injection pump. When the injection flow rate reaches a limit value for temperature adjustment, the injection flow rate is no longer adjusted; instead, the temperature is further adjusted by adjusting the output frequency of the radio frequency signal, until the temperature value fall within the temperature range.

The impedance is adjusted merely by adjusting the injection flow rate of the injection pump. On the premise that the temperature value is maintained within the temperature range, the injection flow rate of the injection pump is further adjusted, to make the impedance value be within the impedance range.

Other technical details of various steps above can be found in the descriptions of the embodiment shown in FIG. 2, and will not be repeated here again.

In the embodiment of the present disclosure, the data protection mode of the radio frequency operation object includes the temperature-based uni-protection mode, the impedance-based uni-protection mode and the temperature- and impedance-based dual-protection mode. Multiple protection modes are provided to improve the flexibility of protection. Corresponding to the data protection modes, the temperature, the impedance, or the temperature and impedance of the radio frequency operation object are detected in real time. In the temperature- and impedance-based dual-protection mode, the temperature is adjusted first, such that the temperature value is adjusted to be within the preset temperature range; and then the impedance is adjusted, such that the impedance value is adjusted to be within the preset impedance range. In the temperature-based uni-protection mode, the temperature value is adjusted to be within the preset temperature range. In the impedance-based uni-protection mode, the impedance value is adjusted to be within the preset impedance range. By the adjustment of the temperature and impedance of the radio frequency operation object, multi-level and sequential adjustment is achieved. As a result, the flexibility of adjustment is increased, the success rate of the radio frequency operation is improved, and equipment damages and personal injuries caused by data abnormality in the radio frequency operation are avoided, thereby improving the safety of the radio frequency operation.

FIG. 4 is a structural schematic diagram of a radio frequency host provided in an embodiment of the present disclosure. For convenience of description, only the parts relevant to the embodiments of the present disclosure are shown. The radio frequency host is a radio frequency host shown in FIGS. 1-3 above. The radio frequency host includes:

a determination module 401, configured to determine a data protection mode of a radio frequency operation object, wherein the data protection mode includes a uni-protection mode and a dual-protection mode;

a detection module 402, configured to detect, in real time, first physical characteristic data and second physical characteristic data of the radio frequency operation object corresponding to the dual-protection mode, when the data protection mode is the dual-protection mode; and an adjustment module 403, configured to adjust the value of the first physical characteristic data and the value of the second physical characteristic data respectively according to the priorities of protection against the first physical characteristic data and the second physical characteristic data, when the value of the first physical characteristic data and the value of the second physical characteristic data exceed their respective preset numerical ranges, to make the value of the first physical characteristic data and the value of the second physical characteristic data be both within their respective preset numerical ranges.

When the data protection mode of the radio frequency operation object is the dual-protection mode, the first physical characteristic data and the second physical characteristic data of the radio frequency operation object corresponding to the dual-protection mode are detected in real time. When the value of the first physical characteristic data and the value of the second physical characteristic data are respectively beyond their respective preset numerical ranges, the value of the first physical characteristic data and the value of the second physical characteristic data are adjusted respectively according to the priorities of protection against the first physical characteristic data and the second physical characteristic data, to make the value of the first physical characteristic data and the value of the second physical characteristic data be both within their respective preset numerical ranges. Through the dual adjustment of two physical characteristic data of the radio frequency operation object in sequence, the success rate of the radio frequency operation is improved, and equipment damages and personal injuries caused by data abnormality in the radio frequency operation are avoided, thereby improving the safety of the radio frequency operation.

Further, the dual-protection mode is a temperature- and impedance-based dual-protection mode, the first physical characteristic data is the temperature, and the second physical characteristic data is the impedance.

The detection module 402 is further configured to detect the temperature and the impedance of the radio frequency operation object in real time.

The priority of protection against the temperature of the radio frequency operation object is higher than the priority of protection against the impedance of the radio frequency operation object.

The adjustment module 403 is further configured to control an injection pump to inject a cooling medium to the radio frequency operation object at a preset temperature adjustment-intended injection flow rate, to make the temperature value of the radio frequency operation object be within the preset first numerical range;

control the output power of the radio-frequency signal, to make the temperature value of the radio frequency operation object be within the first numerical range if the temperature value of the radio frequency operation object is still beyond the first numerical range when the injection flow rate of the injection pump reaches a limit value for temperature adjustment; and control the injection pump to inject the cooling medium to the radio frequency operation object at a preset impedance adjustment-intended injection flow rate, to make the impedance value of the radio frequency operation object be within the preset second numerical range.

The adjustment module 403 is further configured to acquire a preset corresponding relationship between the adjustment amount of the temperature adjustment-intended injection flow rate and the adjustment amount of the temperature value of the radio frequency operation object; query the corresponding relationship according to a difference between a target value for temperature adjustment and a present temperature value of the radio frequency operation object, to obtain an adjustment amount of the temperature adjustment-intended injection flow rate; and obtain the temperature adjustment-intended injection flow rate according to the present injection flow rate and the adjustment amount.

Further, the uni-protection mode includes a temperature-based uni-protection mode and an impedance-based uni-protection mode.

The determination module 401 is further configured to acquire information of the data protection mode set by a user; determine that the data protection mode of the radio frequency operation object is one of the temperature-based uni-protection mode, the impedance-based uni-protection mode, and the temperature- and impedance-based dual-protection mode according to the user's setting when the data protection mode is set by the user; and determine that the data protection mode of the radio frequency operation object is the temperature- and impedance-based dual-protection mode when the data protection mode is not set by the user.

The detection module 402 is further configured to detect the temperature value of the radio frequency operation object in real time when the data protection mode is the temperature-based uni-protection mode; and detect the impedance value of the radio frequency operation object in real time when the data protection mode is the impedance-based uni-protection mode.

In the embodiment of the present disclosure, the data protection mode of the radio frequency operation object includes the temperature-based uni-protection mode, the impedance-based uni-protection mode and the temperature- and impedance-based dual-protection mode. Multiple protection modes are provided to improve the flexibility of protection. Corresponding to the data protection modes, the temperature, the impedance, or the temperature and impedance of the radio frequency operation object are detected in real time. In the temperature- and impedance-based dual-protection mode, the temperature is adjusted first, such that the temperature value is adjusted to be within the preset temperature range; and then the impedance is adjusted, such that the impedance value is adjusted to be within the preset impedance range. In the temperature-based uni-protection mode, the temperature value is adjusted to be within the preset temperature range. In the impedance-based uni-protection mode, the impedance value is adjusted to be within the preset impedance range. By the adjustment of the temperature and impedance of the radio frequency operation object, multi-level and sequential adjustment is achieved. As a result, the flexibility of adjustment is increased, the success rate of the radio frequency operation is improved, and equipment damages and personal injuries caused by data abnormality in the radio frequency operation are avoided, thereby improving the safety of the radio frequency operation.

As shown in FIG. 5, an embodiment of the present disclosure further provides a radio-frequency host, which includes a storage 500 and a processor 600. The processor 600 may be a detector in the above embodiments, or a controller. The storage 500 is, for example, hard drive storage, a non-volatile storage (such as flash memory or other storages that are used to form solid-state drives and are electronically programmable to confine the deletion, etc.), and a volatile storage (such as static or dynamic random access storage), which is not limited in the embodiments of the present disclosure.

The storage 500 stores an executable program code; and the processor 600 is coupled to the storage 500 and configured to call the executable program code stored in the storage, and implement the method for protecting a radio frequency operation object from data abnormality as described above.

Further, an embodiment of the present application further provides a computer-readable storage medium, which can be provided in the radio frequency host in each of the above embodiments, and may be the storage 500 in the embodiment shown in FIG. 5. A computer program is stored in the computer-readable storage medium. When the program is executed by a processor, the method for protecting a radio frequency operation object from data abnormality according to the embodiments as shown in FIGS. 2 and 3 is implemented. Further, the computer-readable storage medium may also be a U disk, a movable hard disk, a read-only memory (ROM), RAM, a magnetic disk, an optical disc and various other media on which program codes can be stored.

Other technical details are described in various embodiments describe above.

It should be noted that for ease of description of the above method embodiments, they are all described as a series of actions. However, it is to be known by those skilled in the art that the present disclosure is not limited to the sequence of actions described, because in the present disclosure, some steps can be done in other sequences or simultaneously. Further, it is to be known by those skilled in the art that embodiments described in the specification are all preferred embodiments, the actions and modules involved therein are not necessarily required for the present disclosure.

In the embodiments described above, emphasis has been placed on the description of various embodiments. Parts of an embodiment that are not described in detail may be found in the description of other embodiments.

The method for protecting a radio frequency operation object from data abnormality, the radio frequency host and the computer readable storage medium provided in the present disclosure are described above. Changes can be made to the specific implementation and the scope of the present application by those skilled in the art according to the idea of the embodiments of the present disclosure. Therefore, the disclosure of this specification should not be construed as a limitation of the present disclosure.

The invention claimed is:

1. A method for protecting a radio frequency operation object from data abnormality, comprising:
determining a data protection mode of the radio frequency operation object, wherein the data protection mode comprises a uni-protection mode and a dual-protection mode;

when the data protection mode is the dual-protection mode, detecting, in real time, first physical characteristic data and second physical characteristic data of the radio-frequency operation object corresponding to the dual-protection mode;

when a value of the first physical characteristic data and a value of the second physical characteristic data are beyond their respective preset numerical ranges, adjusting the value of the first physical characteristic data and the value of the second physical characteristic data respectively according to priorities of protection against the first physical characteristic data and the second physical characteristic data, to make the value of the first physical characteristic data and the value of the second physical characteristic data be both within their respective preset numerical ranges;

wherein the dual-protection mode is a temperature- and impedance-based dual-protection mode, the first physical characteristic data is a temperature, the second physical characteristic data is an impedance, and the step of detecting, in real time, first physical characteristic data and second physical characteristic data of the radio frequency operation object corresponding to the dual-protection mode comprises:
detecting the temperature and impedance of the radio frequency operation object in real time; and
wherein the priority of protection against the temperature of the radio frequency operation object is higher than the priority of protection against the impedance of the radio frequency operation object.

2. The method according to claim 1, wherein the step of adjusting the value of the first physical characteristic data and the value of the second physical characteristic data respectively according to priorities of protection against the first physical characteristic data and the second physical characteristic data, to make the value of the first physical characteristic data and the value of the second physical characteristic data be both within their respective preset numerical ranges, comprises steps of:
controlling an injection pump to inject a cooling medium to the radio frequency operation object at a preset temperature adjustment-intended injection flow rate, to make a temperature value of the radio frequency operation object be within a first numerical range, wherein the first numerical range is the respective preset numerical range of the value of the first physical characteristic data;
stopping controlling of the injection flow rate in case that the temperature value of the radio frequency operation object is still beyond the first numerical range and the injection flow rate of the injection pump reaches a limit value for temperature adjustment, and controlling the output power of the radio frequency signal to make the temperature value of the radio frequency operation object be within the first numerical range, wherein the limit value for temperature adjustment is less than a maximum injection flow rate of the injection pump; and
controlling the injection pump to inject the cooling medium to the radio frequency operation object at a preset impedance adjustment-intended injection flow rate, to make an impedance value of the radio frequency operation object be within a second numerical range, wherein the second numerical range is the respective preset numerical range of the value of the second physical characteristic data.

3. The method according to claim 2, further comprising:

acquiring a preset corresponding relationship between the adjustment amount of the temperature adjustment-intended injection flow rate and the adjustment amount of the temperature value of the radio frequency operation object;

querying the corresponding relationship according to a difference between a target value for temperature adjustment and a current temperature value of the radio frequency operation object, to obtain an adjustment amount of the temperature adjustment-intended injection flow rate; and obtaining the temperature adjustment-intended injection flow rate according to the present injection flow rate and the adjustment amount.

4. The method according to claim 3, wherein the uni-protection mode comprises a temperature-based uni-protection mode and an impedance-based uni-protection mode, and the step of determining a data protection mode of the radio frequency operation object comprises steps of:

acquiring information of the data protection mode set by a user;

determining that the data protection mode of the radio frequency operation object is one of the temperature-based uni-protection mode, the impedance-based uni-protection mode, and the temperature- and impedance-based dual-protection mode according to the user's setting when the data protection mode is set by the user; and determining that the data protection mode of the radio frequency operation object is the temperature- and impedance-based dual-protection mode, when the data protection mode is not set by the user.

5. The method according to claim 4, further comprising, after the step of determining a data protection mode of the radio frequency operation object:

detecting the temperature value of the radio frequency operation object in real time when the data protection mode is the temperature-based uni-protection mode; and detecting the impedance value of the radio frequency operation object in real time when the data protection mode is the impedance-based uni-protection mode.

6. A radio frequency host, comprising:

a determination module, configured to determine a data protection mode of a radio frequency operation object, wherein the data protection mode comprises a uni-protection mode and a dual-protection mode;

a detection module, configured to detect, in real time, first physical characteristic data and second physical characteristic data of the radio-frequency operation object corresponding to the dual-protection mode, when the data protection mode is the dual-protection mode;

an adjustment module, configured to adjust a value of the first physical characteristic data and a value of the second physical characteristic data respectively according to priorities of protection against the first physical characteristic data and the second physical characteristic data, when the value of the first physical characteristic data and the value of the second physical characteristic data are beyond their respective preset numerical ranges, to make the value of the first physical characteristic data and the value of the second physical characteristic data be both within their respective preset numerical ranges;

wherein the dual-protection mode is a temperature- and impedance-based dual-protection mode, the first physical characteristic data is a temperature, the second physical characteristic data is an impedance, and detecting, in real time, first physical characteristic data and second physical characteristic data of the radio frequency operation object corresponding to the dual-protection mode comprises:

detecting the temperature and impedance of the radio frequency operation object in real time; and wherein the priority of protection against the temperature of the radio frequency operation object is higher than the priority of protection against the impedance of the radio frequency operation object.

7. A radio frequency host, comprising:

a storage and a processor, wherein the storage stores an executable program code; and the processor is coupled to the storage, and configured to call the executable program code stored in the storage, and implement the method for protecting a radio frequency operation object from data abnormality according to claim 1.

8. A computer readable storage medium, storing a computer program, wherein when the computer program is executed by a processor, the method for protecting a radio frequency operation object from data abnormality according to claim 1 is implemented.

* * * * *